United States Patent [19]

Silvis et al.

[11] Patent Number: 4,661,644

[45] Date of Patent: Apr. 28, 1987

[54] BROMINATED EPOXYAROMATIC COMPOUNDS

[75] Inventors: Harry C. Silvis; Abel Mendoza, both of Midland, MI

[73] Assignee: The Dow Chemical Company, Midland, Mich.

[21] Appl. No.: 812,476

[22] Filed: Dec. 23, 1985

Related U.S. Application Data

[63] Continuation-in-part of Ser. No. 773,685, Sep. 9, 1985.

[51] Int. Cl.[4] .................... C07C 39/17; C07D 303/02
[52] U.S. Cl. .................... 568/723; 568/744; 549/516; 549/517
[58] Field of Search ............... 568/723, 744, 779, 730; 549/512, 516, 517, 559

[56] References Cited

U.S. PATENT DOCUMENTS

| | | | |
|---|---|---|---|
| 2,841,595 | 7/1958 | Pezzaglia | 549/517 |
| 3,929,908 | 12/1975 | Orlando | 568/730 |
| 3,956,403 | 5/1976 | Orlando | 568/730 |
| 3,957,832 | 5/1976 | Bressler et al. | 568/744 |
| 4,058,570 | 11/1977 | Kinson et al. | 568/730 |
| 4,221,893 | 9/1980 | Behar et al. | 568/726 |
| 4,284,573 | 8/1981 | Arnett | 549/517 |

FOREIGN PATENT DOCUMENTS

| | | | |
|---|---|---|---|
| 229317 | 7/1960 | Australia | 549/517 |
| 232484 | 1/1961 | Australia | 549/517 |
| 687375 | 5/1964 | Canada | 549/517 |
| 14586 | 1/1982 | Japan | 549/517 |
| 227873 | 12/1984 | Japan | 549/517 |

*Primary Examiner*—Werren B. Lone

[57] ABSTRACT

Novel ring-brominated derivatives of the diepoxides of tetraalkyl dihydroxydiaromatic compounds, e.g., the diglycidyl ether of 3,5-dibromo-4-(2-(2-bromo-4-hydroxy-3,5-dimethylphenyl)ethyl)-2,6-dimethylphenol.

20 Claims, No Drawings

BROMINATED EPOXYAROMATIC COMPOUNDS

CROSS-REFERENCE TO RELATED APPLICATION

This is a continuation-in-part of application Ser. No. 773,685, filed Sept. 9, 1985.

BACKGROUND OF THE INVENTION

The present invention relates to epoxide derivatives of brominated aromatic compounds. More specifically, it relates to ring brominated epoxyaromatic compounds.

It is known to prepare brominated alkyl phenols. See, e g., *Can. J. Chem.*, Vol. 61, pp. 1045–1052 (1983); and *Russian Chemical Reviews*, Vol. 32, pp. 75–93 (1963). Brominated tetraalkylhydroxyaromatic compounds having 2 aromatic rings also have been prepared in the past. Brominated tetraalkyl biphenols having the benzene rings directly linked have been prepared from tetraalkyl diphenoquinones; see, e.g., U.S. Pat. Nos. 3,929,908; 3,956,403 and 4,058,570. However, when brominating compounds wherein the aromatic rings have an alkylene bridge, the products typically do not have bromine on the aromatic rings. For example, Bradley and Sanders, *J. Chem. Soc.*, Vol. 1962, pp. 480–486 (1962) disclose the reaction of 3,3',5,5'-tetra-t-butylstilbenequinone with HBr to yield α,β-dibromo-4,4'-dihydroxy-3,3',5,5'-tetra-t-butyldibenzyl. Kharasch and Joshi, *J. Org. Chem.*, Vol. 22, pp. 1435–1438 (1957) disclose the reaction of bromine with 4,4'-methylenebis(2,6-ditertiarybutylphenol) in the presence of acetic acid to give 1-bromo-1,1-bis-(3,5-ditertiarybutyl-4-hydroxyphenyl)methane.

The compound 2,2'-(1,2-ethanediyl)bis(3,5-dibromo-4,6-dimethylphenol) has been prepared by the hydrogenation of 4',5,6',7-tetrabromo-3',5',6,8-tetramethyl-3,4-dihydrospiro(2H-1-benzopyran-2,1'-[3,5]cyclohexadien)-2'-one; Ann., Vol. 548, pp. 48–77 at page 57 (1939); and by the bromination of 2,2'-(1,2-ethanediyl)-bis(4,6-dimethylphenol).

In view of the deficiencies of prior art bromination methods, it would be desirable to have a simple method for the preparation of novel ring brominated polymethylene-bridged di(dialkylhydroxyaromatic) compounds having terminal para hydroxyl moieties. Such a method would be useful in the preparation of novel epoxy derivatives of said compounds.

SUMMARY OF THE INVENTION

The compounds of the present invention are novel epoxy derivatives of ring-brominated polymethylene-bridged di(dialkylhydroxyaromatic) compounds. The epoxides have terminal para epoxy moieties and at least one bromine atom meta relative to at least one of said epoxy moieties. The ring-brominated novel epoxy compounds of the invention are highly stable and are useful as chemical intermediates in the preparation of valuable chemical compounds. For example, the compounds of the present invention can be employed in the preparation of cured epoxy resins.

DETAILED DESCRIPTION OF THE INVENTION

The compounds of the present invention are prepared by contacting a tetraalkyl ring-brominated dihydroxydiaromatic polymethylene-bridged compound (hereinafter brominated TDDPC) having terminal para hydroxyl moieties and a haloalkylene oxide under reaction conditions.

A. Preparation of starting material brominated TDDPC's

The brominated TDDPC starting material can be prepared by contacting in a liquid reaction medium under reaction conditions a brominating agent, a TDDPC and, optionally, a bromination catalyst, the conditions being such that a di-, tri- or tetra ring-brominated tetraalkyl dihydroxydiaromatic polymethylene-bridged compound is formed.

Preferred TDDPC's are represented generally by the formula:

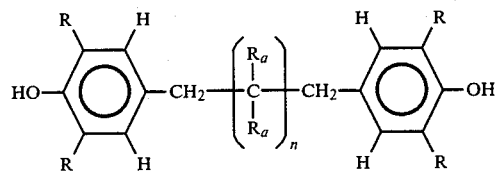

wherein n is zero or a positive integer, each $R_a$ independently is H or alkyl of up to about 12 carbon atoms, and each R independently is a primary or secondary alkyl moiety of up to about 6 carbon atoms. Preferably, n is zero or a positive integer of up to about 12, each $R_a$ independently is H or alkyl of up to about 6 carbon atoms, and each R independently is alkyl of up to about 3 carbon atoms. R most preferably is methyl, $R_a$ most preferably is H, and n most preferably is zero. It should be noted that the process of the present invention can be employed to put additional bromine atoms on partially brominated TDDPC's.

A brominating agent is employed in the preparation of the brominated TDDPC. While it may be possible to employ known brominating agents which are useful for the bromination of aromatic rings, bromine is the preferred brominating agent when high purity products are desired. The amount of bromine to employ depends upon (1) the amount of bromine in the product desired, and (2) whether a catalyst is employed. In general, less bromine is required when a catalyst is employed. For example, if the dibromo-product is desired, then stoichiometry would indicate that at least about 2 moles of bromine atoms are required per mole of substrate compound to be brominated. Typically, with a catalyst, a stoichiometric excess of bromine ranging from about 0 to about 25 percent or more is employed; preferably, a stoichiometric excess ranging from about 5 to about 15 percent is employed. Typically, up to about 12 moles of bromine are employed per mole of TDDPC in the production of tetra-brominated products when operating without a catalyst. Smaller excesses of bromine typically require longer reaction times. Similarly, if a brominating agent is employed which is not bromine, the amount of said agent to be employed should provide bromine in the quantities stated hereinabove.

A bromination catalyst is optionally employed in the bromination process. Friedel-Crafts catalysts are preferred, and are well known. Examples of bromination catalysts include the halides of metals such as iron, aluminum, and tin. Examples of preferred catalysts include aluminum bromide and aluminum chloride, with ferric chloride being most preferred. The catalyst is employed in catalytic quantities. Preferably, the amount of catalyst employed ranges from about 0.1 to about 5 weight percent of catalyst based on the mass of aromatic compound employed. Larger amounts of catalyst may be employed, but may be economically impractical. The catalyst may be employed in a variety of forms.

A reaction medium advantageously is employed in the bromination process. The reaction medium functions to solubilize the reactants and reaction products, and to aid in heat transfer. While the amount of reaction medium employed may range widely, the amount of reaction medium to be employed generally is indicated by practical considerations, and typically ranges from about 8 to about 20 moles of reaction medium per mole of aromatic compound. Preferably, from about 10 to about 15 moles of reaction medium are employed per mole of aromatic compound. Typical solvents include the perhalogenated lower alkanes. Carbon tetrachloride is the preferred solvent when no catalyst is employed. Methylene chloride is preferred when a catalyst is employed.

The order of addition of the reactants is not critical. However, according to a preferred bromination process, a brominating agent is slowly added to a mixture comprising a reaction medium, a TDDPC, and, optionally, a bromination catalyst. When the addition of the brominating agent is complete, the resulting reaction mixture typically is brought to elevated temperature until the reaction is completed.

The initial addition temperature, i.e., the temperature of the reaction mixture during the period of addition of the brominating agent thereto, typically is a temperature at which the reaction mixture is a liquid. Preferably, the initial addition temperature is up to about 30° C. More preferably, the addition temperature is from about 20° C. to about 30° C. Most preferably, for the sake of convenience, ambient temperature is employed.

As stated hereinabove, when the addition of the brominating agent to the reaction mixture is complete, the total reaction mixture can be heated to elevated temperature in order to assure complete bromination. Typically, the total reaction mixture is heated to reflux temperature and said temperature is maintained until the reaction is complete. Completion of the reaction can be observed by following the rate of evolution of hydrogen bromide from the reaction mixture, i.e., the reaction is complete when the rate of hydrogen bromide evolution falls to zero. Ordinarily, the reaction will proceed at atmospheric pressure or higher, but subatmospheric pressure can be employed if desired.

The total reaction time of from 1 to about 100 hours, depending primarily on the aromatic reacting, is generally adequate for complete reaction under the conditions of the invention. Typically, a total reaction time of up to about 20 hours will be sufficient to produce high yields of high assay products. In some cases, bromination may be complete in 3 hours or less. It is desirable to add the brominating agent to the reaction mixture at a sufficiently slow rate to minimize loss of bromine and reaction medium, and to permit the desired low addition temperature to be maintained under conditions of control and safety.

When the reaction is carried out as described hereinabove, a brominated TDDPC will be formed. Preferred brominated TDDPC's are represented generally by the following formula:

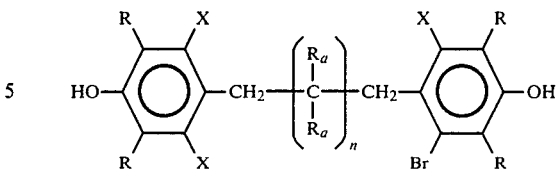

wherein n, R, and $R_a$ are as described hereinabove, and wherein each X independently is Br or H. Preferably, at least one X moiety is Br. Most preferably, two or three X moieties are Br. Surprisingly, the polymethylene-bridge does not cleave under bromination conditions, nor do the brominated TDDPC's contain benzyl bromine atoms.

The reaction mixture resulting from carrying out the bromination process can be processed by a variety of known work-up procedures to isolate the brominated products. The crude reaction mixture, which may contain the brominated products, excess reaction medium and catalyst, can, for instance, be subjected to stripping either at atmospheric pressure or preferably under reduced pressure to the point of constant weight of the residue, or the insoluble product can be filtered. The crude product which is thus isolated may be further purified, for instance, by recrystallization or by digestion with a recovery medium such as acetone, toluene, or dilute hydrochloric acid. This isolation method by stripping is fast, simple and gives reliable yield data and relatively pure product. It is preferred to employ a work-up method which neutralizes bromine. The yield of pure product, i.e., the numerical product of conversion of TDDPC, selectivity to the desired product, and purity of the desired product, typically is at least about 50 mole percent. Preferably, the yield is at least about 60 mole percent, and more preferably, the yield is at least about 75 mole percent.

It is generally possible to predict the product(s) which will result from application of this perbromination process under optimum reaction conditions to any particular starting material. The general rule is that every nuclear hydrogen atom of the aromatic compound will be replaced by a bromine atom if the reaction is carried to completion, that is, until the evolution of hydrogen bromide has stopped. This level of bromination may be reached by proper adjustment of reaction temperature, catalyst concentration and reaction time. The bromination process is continued until such time as the sampling indicates that the desired degree of bromination has been reached, or the bromination reaction may be continued until evolution of hydrogen bromide has substantially ceased.

B. Preparation of the epoxy compounds of the present invention

As stated hereinabove, the compounds of the present invention are prepared by contacting a brominated TDDPC with a haloalkylene oxide under reaction conditions such that there is formed an epoxy derivative of a brominated TDDPC.

Typical haloalkylene oxides are represented generally by the formula

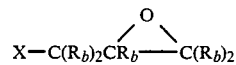

wherein X is halo, and wherein each $R_b$ independently is H or an aliphatic or inertly-substituted aliphatic moiety of up to about 25 carbon atoms. Preferably, each $R_b$ is H, and X is chlorine or bromine, with chlorine being more preferred. Examples of haloalkylene oxides desirably employed in the process include chloropropylene oxide, iodopropylene oxide, methyl epichlorohydrin, methyl epibromohydrin, methyl epiiodohydrin, chlorobutylene oxide, bromopropylene oxide, and the like of up to about 5 carbon atoms, with chloropropylene oxide (epichlorohydrin) being preferred. Mixtures of haloalkylene oxides ca be employed.

The reaction conditions employed for the addition of haloalkylene oxides to hydroxyl-containing or active-hydrogen-containing compounds are well-known. See, e.g., *Handbook of Epoxy Resins*, by Lee and Neville, McGraw-Hill (1967); and U.S. Pat. No. 4,284,573; the teachings of each of which are incorporated by reference. Said known conditions are advantageously employed in the preparation of the compounds of the present invention. Typically, for example, from about 3 to about 50 moles of haloalkylene oxide are employed per mole of active hydrogen atoms in the brominated TDDPC, with a preferred amount being from about 10 to about 25 moles per mole. Larger or smaller amounts can be employed if desired. The contacting can be performed at any combination of temperature and pressure at which the desired reaction will proceed. Typically, the contacting is performed at elevated temperature. Preferably, the temperature is from about 60° C. to about the boiling point of the haloalkylene oxide. Ambient pressure is preferred for the sake of convenience.

A catalyst is optionally employed, and can be selected from known catalysts for this reaction, including the wide range of catalysts mentioned in the references cited previously herein. Examples of preferred catalysts include, for example, tetraethylammonium bromide, ethyltriphenyl phosphonium acetate and the like.

When the brominated TDDPC and haloalkylene oxide are contacted as described hereinabove, an epoxy resin is produced which is an epoxy derivative of the brominated TDDPC. Examples of typical epoxy resins of the present invention are represented by the formula:

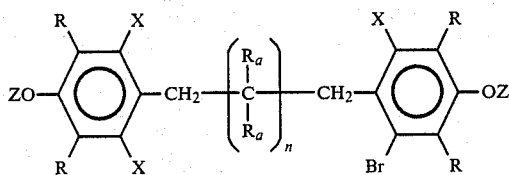

wherein n is zero or a positive integer, each X independently is bromine or hydrogen, each $R_a$ independently is hydrogen or alkyl of up to about 12 carbon atoms, each R independently is a primary or secondary alkyl moiety of up to about 6 carbon atoms, and each Z independently is a moiety having a terminal epoxide moiety. The Z moieties correspond to the structure of the haloalkylene oxide employed. For example, when epichlorohydrin is the haloalkylene oxide, Z is a moiety of the formula:

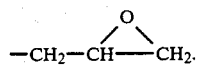

The epoxy resins of the present invention can be cured to form novel epoxy polymers having surprisingly improved properties. The epoxy resins can be cured using well-known techniques. The novel cured resins of the present invention typically are prepared by heating the polyepoxide compounds with a curing agent, typically at a temperature of from about 0° C. to about 300° C., and preferably from about 25° C. to about 250° C.

As curing agents there can, for example, be mentioned: amines or amides such as aliphatic, cycloaliphatic or aromatic primary, secondary and tertiary amines, for example, monoethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3, bis(4'-amino-3-methylcyclohexyl)methane, 2,2-bis(4'-aminocyclohexyl)propane, 3,5,5-trimethyl-3-(aminomethyl)cyclohexylamine ("isophoronediamine"), N-aminoethylpiperazine, Mannich bases, such as 2,4,6-tris(dimethylaminomethyl)phenol; m-phenylenediamine, p-phenylenediamine, bis(p-aminophenyl)-methane, bis(p-aminophenyl)sulfone and m-xylylenediamine; adducts of acrylonitrile or monoepoxides such as ethylene oxide or propylene oxide to polyalkylenepolyamines such as diethylenetriamine or triethylenetetramine; adducts of polyamines such as excess diethylenetriamine or triethylenetetramine, and polyepoxides such as diphenylmethane polyglycidyl ethers; ketimines, for example, from acetone or methyl ethyl ketone and bis(p-aminophenyl)methane; adducts of monophenols or polyphenols and polyamines; polyamides, especially those from aliphatic polyamines, such as diethylenetriamine or triethylenetetramine and dimerized or trimerized unsaturated fatty acids such as dimerized linseed oil fatty acid ("VERSAMID"); polymeric polysulfides ("THIOKOL"); dicyandiamide; aniline-formaldehyde resins; polyhydric phenols, for example, resorcinol, 2,2-bis(4-hydroxyphenyl)propane or phenol-formaldehyde resins; boron trifluoride and its complexes with organic compounds, such as $BF_2$ ether complexes and $BF_3$ amine complexes, for example, $BF_3$-monoethylamine complex; acetoneacetanilide-$BF_3$ complex; phosphoric acid, triphenylphosphite, polybasic carboxylic acids and their anhydrides, for example, phthalic anhydride, tetrahydrophthalic anhydride, hexahydrophthalic anhydride, 4-methylhexahydrophthalic anhydride, 3,6-endomethylene-tetrahydrophthalic anhydride, methyl-3, 6-endomethylene-tetrahydrophthalic anhydride, (methylnadicanhydride), 3,4,5,6,7,7-hexachlor-3,6-endomethylene-tetrahydrophthalic anhydride, succinic anhydride, adipic anhydride, azelaic anhydride, sebacic anhydride, maleic anhydride, dodecenyl-succinic anhydride; pyromellitic dianhydride or mixtures of such anhydrides.

It is particularly advantageous to use curing agents which in themselves yield molding materials of good electrical properties, such as especially cycloaliphatic dicarboxylic acid anhydrides such as, for example, $\Delta^4$-tetrahydrophthalic anhydride or hexahydrophthalic anhydride, or cycloaliphatic polyamines such as, for example, 2,2-bis(4'-aminocyclohexyl)propane or "isophoronediamine".

It is furthermore possible to use cure accelerators during the cure, and in particular when using polyamides, polymeric polysulfides, dicyandiamide or polycarboxylic acid anhydrides as curing agents; such accelerators are, for example, tertiary amines, their salts or quaternary ammonium compounds, for example, 2,4,6-tris(dimethylaminomethyl)phenol, benzyldimethylamines, 2-ethyl-4-methylimidazole or triamylammonium phenolate; or alkali metal alcoholates such as, for example, sodium hexanetriolate.

The expression "cure" as used here denotes the conversion of the above adducts containing epoxide groups into insoluble and infusible cross-linked products, and in particular as a rule with simultaneous shaping to give shaped articles such as castings, pressings or laminates, or to give two-dimensional structures such as coatings, lacquer films or adhesive bonds.

If desired, it is possible to add active diluents such as, for example, styrene oxide, butylglycidyl ether, isooctylglycidyl ether, phenylglycidyl ether, cresylglycidyl ether or glycidyl esters of synthetic highly branched mainly tertiary aliphatic monocarboxylic acids ("CARDURA E"), or cycloaliphatic monoepoxides such as 3-vinyl-2,4-dioxaspiro (5,5)-9,10-epoxyundecane.

The adducts according to the invention can furthermore be mixed with other curable diepoxide or polyepoxide compounds. As such that can, for example, be mentioned: polyglycidyl ethers of polyhydric alcohols such as 1,4-butanediol, polyethylene glycols, polypropylene glycols or 2,2-bis(4'-hydroxycyclohexyl)propane; polyglycidyl ethers of polyhydric phenols such as 2,2-bis(4'-hydroxyphenyl)-propane, 2,2-bis(4'-hydroxy-3,5'-dibromophenyl)-propane, bis(4-hydroxyphenyl)sulfone, 1,1,2,2-tetrakis(4-hydroxyphenyl)ethane or condensation products of formaldehyde with phenols produced in an acid medium, such as phenol novolacs or cresol novolacs; polyglycidyl esters of polycarboxylic acids such as, for example, phthalic acid diglycidyl ester, tetrahydrophthalic acid diglycidyl ester or hexahydrophthalic acid diglycidyl ester; triglycidyl isocyanurate, N,N'-diglycidyl-5,5-dimethyl hydantoin, or aminopolyepoxides such as are obtained by dehydrohalogenation of the reaction products of epihalogenohydrin and primary or secondary amines such as aniline or 4,4'-diaminodiphenylmethane; also alicyclic compounds containing several epoxide groups, such as vinylcyclohexene-diepoxide, dicyclopentadienediepoxide, ethylene glycol-bis(3,4-epoxytetrahydrodicyclopentadien-8-yl)ether, (3,4-epoxycyclohexylmethyl)-3,4-epoxycyclohexanecarboxylate, (3',4'-epoxy-6'-methylcyclohexylmethyl)-3,4-epoxy-6-methylcyclohexanecarboxylate, bis(cyclopentyl)ether diepoxide or 3-(3',4'-epoxycyclohexyl)-2,4-dioxaspiro-(5,5)9,10-epoxyundecane.

The subject matter of the present invention therefore also includes curable mixtures which are suitable for the manufacture of shaped articles including two-dimensional structures and which contain the so-called "advanced" adducts containing epoxide groups according to the invention, optionally together with other diepoxide or polyepoxide compounds and also curing agents for epoxide resins such as polyamines or polycarboxylic acid anhydrides.

The compounds of the invention, or their mixtures with other polyepoxide compounds and/or curing agents, can furthermore be mixed, at any state before cure, with usual modifiers such as extenders, fillers and reinforcing agents, pigments, dyestuffs, organic solvents, plasticizers and the like.

As extenders, reinforcing agents, fillers and pigments which can be employed in the curable mixtures according to the invention there can, for example, be mentioned: coal tar, bitumen, glass fibers, boron fibers, carbon fibers, cellulose, polyethylene powder, polypropylene powder, mica, asbestos, quartz powder, slate powder, aluminum oxide trihydrate, chalk powder, gypsum, antimony trioxide, bentones, silica aerogel ("AEROSIL"), lithopone, barite, titanium dioxide, carbon black, graphite, iron oxide or metal powder such as aluminum powder or iron powder.

The following are, for example, suitable as organic solvents for modifying the curable mixtures: toluene, xylene, n-propanol, butyl acetate, acetone, methyl ethyl ketone, diacetone-alcohol, ethylene glycol, monomethyl ether, monoethyl ether and monobutyl ether.

Dibutyl, dioctyl and dinonyl phthalate, tricresyl phosphate, trixylenyl phosphate and also polypropylene glycols can, for example, be employed as plasticizers for modifying the curable mixtures.

Especially for use in the lacquer field, the new adducts containing epoxide groups can furthermore be partially or completely esterified in a known manner with carboxylic acids, such as especially higher unsaturated fatty acids. It is furthermore possible to add other curable synthetic resins, for example, phenoplastics or aminoplastics, to such lacquer resin formulations.

It is furthermore also possible to add other usual additives, for example, agents for conferring thixotropy, flow control agents such as silicones, cellulose acetobutyrate, polyvinyl butyral, waxes, stearates and the like (which are in part also used as mold release agents) to the curable mixtures.

The curable mixtures can be manufactured in the usual manner with the aid of known mixing equipment (stirrers, kneaders, rollers and the like).

The curable epoxide resin mixtures referred to hereinabove can be employed in the fields of surface protection, the electrical industry, laminating processes and the building industry. They can be used in a formulation which is in each case suited to the particular end use, in the unfilled or filled state, optionally in the form of solutions or emulsions, as paints, lacquers, sintering powders, compression molding compositions, dipping resins, casting resins, injection molding formulations, impregnating resins and adhesives, as tool resins, laminating resins, sealing and filling compositions, floor covering compositions and binders for mineral aggregates.

A main field of application lies in the field of compression molding powders and of sintering powders. Here the epoxide resin powder mixtures can be processed without pressure or with pressure, according to known processes such as fluidized bed sintering, electrostatic fluidized bed sintering, spraying, electrostatic spraying, compression molding and the like.

SPECIFIC EMBODIMENTS

The following Preparations, Examples and Comparative Experiments are given to illustrate the invention and should not be construed as limiting its scope. All parts and percentages are by weight unless otherwise indicated.

Preparation 1—Preparation of
4,4'-(1,2-Ethanediyl)bis(3-bromo-2,6-dimethylphenol)
(Dibromotetramethylbisphenol E)

A 20.0-g (0.074 mole) portion of tetramethylbisphenol E is suspended in 75 ml of $CCl_4$. A 4.2-ml portion of bromine (0.082 mole) is added at 23° C.–25° C., and the mixture is heated to reflux. All of the bromine has reacted by this time. Analysis by gas chromatography (GC) and nuclear magnetic resonance (NMR) indicates the following composition: 42 area percent starting material, 14 area percent monobromotetramethylbisphenol E, and 43 area percent dibromotetramethylbisphenol E. After adding 4.2 more ml of bromine, the mixture is refluxed for 1.5 hours and analyzed by gas chromatography; the following composition is obtained: 2 area percent starting material, 7 area percent monobrominated product, 90 area percent dibrominated product, and 1 area percent tribrominated material. Cooling of the slurry to 25° C. and filtration of the insoluble solid gives 29.2 g of a brown solid which melts at 191° C.–194° C. Recrystallization from toluene gives a solid which melts at 194° C.–197° C. and has the following composition: 5 area percent monobromo, 93 area percent dibromo, and 2 area percent tribromotetramethylbisphenol E. The nuclear magnetic resonance spectrum is consistent with the proposed structure: $^1$H MR (acetone $d_6$) δ: 2.20 (s, 6H, —CH$_3$), 2.36 (s, 6H, —CH$_3$), 2.86 (s, 4H, —CH$_2$—), 6.88 (s, 2H, —CH), and 7.35 (s, 2H, —OH).

Preparation 2—Preparation of 3,5-Dibromo-4-(2-(2-bromo-4-hydroxy-3,5-dimethylphenyl)ethyl)-2,6-dimethylphenol (Tribromotetramethylbisphenol E)

A 12.5-g (0.046 mole) portion of tetramethylbisphenol E is suspended in 100 ml of CCl$_4$, and 12.0 ml (0.234 mole) of bromine is added at 23° C.–25° C. After refluxing the mixture for 1 hour, the following composition is observed: 16 area percent dibromo, 77 area percent tribromo, and 7 area percent tetrabromotetramethylbisphenol E. The unreacted bromine is removed by distillation. More CCl$_4$ is added (50 ml), and the slurry is cooled to 25° C. Filtration of the insoluble solid affords 18.2 g of a brown solid which melts at 249° C.–255° C. Recrystallization from toluene affords a gray-brown solid which melts at 257° C.–262° C., and has the following composition: 6 area percent dibromo, 78 area percent tribromo, and 16 area percent tetrabromotetramethylbisphenol E. It has the following nuclear magnetic resonance spectrum: $^1$H NMR (DMSO $d_6$)δ: 2.12 (s, 3H), 2.28 (s, 9H), 3.20 (s, 4H), and 6.90 (s,1H).

Preparation 3—Preparation of 4,4'-(1,2-ethanediyl)bis(3,5-dibromo-2,6-dimethylphenol) (Tetrabromotetramethylbisphenol E)

A 27.1-g (0.1 mole) portion of tetramethylbisphenol E is suspended in 100 ml of CCl$_4$. A 60-ml (1.17 mole) portion of bromine is added dropwise while keeping the temperature below 30° C. using a water bath for cooling. Immediate evolution of HBr is observed. The mixture is brought to reflux for 2 hours. The excess bromine is removed by distillation with the aid of 200 ml of CCl$_4$ The mixture is cooled to 25° C., and the insoluble solid is filtered. This affords 52.0 g of brown solid which melts at 290° C.–297° C. Purification of the insoluble solid involves suspending it in 100 ml of acetone, refluxing for 1 hour, cooling to 25° C., and filtering the insoluble solid. A white solid is obtained, 46.0 g, which melts at 295° C.–297° C. and has the following composition: 75 area percent tetrabromo and 25 area percent tribromotetramethylbisphenol E. The $^1$H NMR spectrum (DMSO $d_6$) has a small singlet at 2.12 δ and 2 major peaks, a singlet at 2.26 δ, and a singlet at 3.20 δ, in a ratio of 3 to 1. This spectrum is consistent with the proposed structure.

Preparation 4—Bromination Using a Friedel-Crafts Catalyst

A 136-g (0.5 mole) portion of tetramethylbisphenol E is suspended in 1,400 ml of CH$_2$Cl$_2$. Following the addition of 2.0 g of FeCl$_3$, 86 ml (1.65 mole) of bromine is added at 20° C.–24° C. After refluxing the mixture for 2 hours all of the bromine had reacted. A portion of the solvent, 300 ml, is removed by distillation, and the slurry is cooled to 25° C. Filtration of the insoluble solid affords 262 g of a light brown solid which has the following composition: 8 area percent dibromo, 58 area percent tribromo and 34 area percent tetrabromotetramethylbisphenol E. The $^1$H NMR spectrum is consistent with this composition.

Comparative Experiment 1—Not an embodiment of the present invention

Bromination of Tetramethylbisphenol F

A 25.6-g portion of tetramethylbisphenol F (0.1 mole) is suspended in 125 ml of carbon tetrachloride, and the slurry is cooled to 5° C. A 6-ml portion of bromine (0.12 mole) is added dropwise, and the mixture is stirred for 15 minutes. All of the bromine reacts. Analysis of the mixture by gas chromatography indicates that >90 percent of the starting material reacts. The major product formed is 4-bromo-2,6-dimethylphenol, which is identified by comparison with an authentic sample; a number of other cleavage products are formed. Addition of 6 more ml of bromine gives complete cleavage of the tetramethylbisphenol F.

Comparative Experiment 2—Not an embodiment of the present invention

Bromination of Tetramethylbisphenol A

A 14.2-g portion of tetramethylbisphenol A (0.05 mole) is suspended in 100 ml of carbon tetrachloride, and the slurry is cooled to 5° C. A 3-ml portion of bromine (0.06 mole) is added dropwise, and the reaction is analyzed by gas chromatography. More than 60 percent of the starting material reacts, forming two major products, one of them being 4-bromo-2,6-dimethylphenol. After stirring at 25° C. for 2 hours, the insoluble product is filtered, 5.5 g, and is identified as tetramethylbisphenol A. The carbon tetrachloride solution has 4-bromo-2,6-dimethylphenol as the main component, as identified by gas chromatography and nuclear magnetic resonance, and by comparison with an authentic sample.

The preceding Preparations and Comparative Experiments surprisingly indicate that TDDP compounds having a polymethylene-bridge can be brominated on the aromatic rings, whereas similar compounds having only one linking carbon atom do not ring-brominate.

EXAMPLE 1

To a slurry of 25 g of brominated bisphenol E (70 percent tribromo, 18 percent tetrabromo, 12 percent dibromo) in 250 ml of epichlorohydrin plus 30 ml of isopropanol at approximately 80° C. is added 19.6 g of 50 percent weight/weight NaOH in water over a two-hour period. After the caustic addition, the reaction temperature is maintained at approximately 80° C. for 2 hours. After cooling, the reaction mixture is diluted with approximately 200 ml of CH$_2$Cl$_2$ and is filtered to remove NaCl. Upon evaporation of the $CH_2Cl_2$, the filtrate yields white crystals. Additional material is obtained by rotoevaporation of the epichlorohydrin/isopropanol. The total yield of product is 23.8 g (78 percent).

The initial solid has a melting point of 197° C.–200° C. and an epoxide equivalent weight of 315.9 g. The second solid has a melting point of 171° C.–175° C. and an epoxide equivalent weight of 309 g. These data, along with nuclear magnetic resonance spectra, suggest that the initial solid is a mixture of tri- and tetrabromotetramethylbisphenol E-diglycidyl ether, while the second solid is a mixture of di- and tribromotetramethylbisphenol E-diglycidyl ether.

Comparative Experiment 3

The diglycidyl ether of tetrabromobisphenol A, 6.00 g (available from The Dow Chemical Company under the name DER ® 542), is cured with 1.127 g diaminodiphenylsulfone. The cured resin is maintained at 265° C. for 1 hour in a convection oven. The resin is observed to lose >50 percent of its weight.

EXAMPLE 2

The first product of Example 1 is employed in the procedure of Comparative Experiment 3 as a replacement for the diglycidyl ether of tetrabromobisphenol A. The resin loses no weight after 1 hour.

A comparison of the results of Example 2 and Comparative Experiment 3 indicates that the resin of Example 2 exhibits unexpectedly improved thermal stability.

What is claimed is:

1. A compound of the formula:

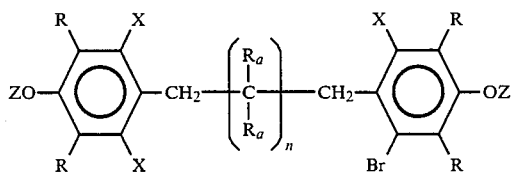

wherein n is zero or a positive integer, each X independently is bromine or hydrogen, each $R_a$ independently is hydrogen or alkyl of up to about 12 carbon atoms, each R independently is a primary or secondary alkyl moiety of up to about 6 carbon atoms, and each Z independently is a moiety having a terminal epoxide moiety.

2. A compound of claim 1 wherein each R has up to about 3 carbon atoms, and wherein each independently is a moiety of the formula:

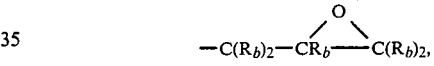

wherein each $R_b$ is hydrogen or an aliphatic or inertly-substituted aliphatic moiety of up to about 25 carbon atoms.

3. A compound of claim 1 wherein each R is a primary alkyl moiety.

4. A compound of claim 2 wherein each $R_a$ has up to about 6 carbon atoms.

5. A compound of claim 2 wherein n is zero, and each $R_b$ is hydrogen.

6. A compound of claim 5 wherein at least one X moiety is bromine.

7. A compound of claim 6 wherein each R is a primary alkyl moiety of up to about 3 carbon atoms.

8. A compound of claim 7 wherein each R is methyl.

9. A compound of claim 8 wherein each X is bromine.

10. A compound of claim 8 wherein at least two X moieties are bromine.

11. The diglycidyl ether of 3,5-dibromo-4-(2-(2-bromo-4-hydroxy-3,5-dimethylphenyl)ethyl)-2,6-dimethylphenol.

12. A composition comprising an adduct of:
   (a) a composition of claim 1;
   (b) a curing agent for epoxy resins; and, optionally,
   (c) a curing catalyst.

13. A composition of claim 12 wherein component (a) has up to about 3 carbon atoms for each R.

14. A composition of claim 12 wherein each Z independently is a moiety of the formula $$-C(R_b)_2-CR_b\underset{\diagdown O \diagup}{\phantom{-}}C(R_b)_2,$$

wherein each $R_b$ is hydrogen or an aliphatic or inertly-substituted aliphatic moiety of up to about 25 carbon atoms.

15. A composition of claim 14 wherein each $R_b$ is hydrogen.

16. A composition of claim 12 wherein n is zero.

17. A composition of claim 12 wherein at least one X is bromine.

18. A composition of claim 12 wherein at least two X moieties are bromine.

19. A composition of claim 12 wherein one X is hydrogen.

20. A composition of claim 12 wherein each R is methyl.

* * * * *

UNITED STATES PATENT AND TRADEMARK OFFICE
CERTIFICATE OF CORRECTION

PATENT NO. : 4,661,644

DATED : April 28, 1987

INVENTOR(S) : Harry C. Silvis; Abel Mendoza

It is certified that error appears in the above-identified patent and that said Letters Patent is hereby corrected as shown below:

Col. 5, line 12, "ca" should read -- can --.

Col. 9, line 20, "MR" should read -- NMR --;
line 57, insert a period after "$CCl_4$".

Col. 10, line 54, "TDDC" should read -- TDDPC --.

Col. 11, line 50, insert -- Z -- between "each" and "independently".

Signed and Sealed this

First Day of November, 1988

Attest:

DONALD J. QUIGG

Attesting Officer

Commissioner of Patents and Trademarks